United States Patent [19]

Barnette et al.

[11] 3,987,100

[45] Oct. 19, 1976

[54] CYCLOHEXANE OXIDATION IN THE PRESENCE OF BINARY CATALYSTS

[75] Inventors: Willie Jon Barnette; Donald Leo Schmitt, both of Orange; Jesse Oris White, Fredericksburg, all of Tex.

[73] Assignee: E. I. Du Pont de Nemours and Company, Wilmington, Del.

[22] Filed: Apr. 11, 1974

[21] Appl. No.: 459,936

[52] U.S. Cl. .................. 260/586 P; 260/586 R; 260/610 B; 260/631 R
[51] Int. Cl.² ................. C07C 45/02; C07C 27/12; C07C 27/04
[58] Field of Search ......... 260/631 R, 586 P, 610 B, 260/586 R

[56] References Cited
UNITED STATES PATENTS

| | | | |
|---|---|---|---|
| 2,223,494 | 12/1946 | Loder | 260/586 P |
| 2,825,742 | 3/1958 | Schueler et al. | 260/631 R |
| 2,851,496 | 9/1958 | Cates et al. | 260/610 B |
| 2,938,924 | 5/1960 | Simon et al. | 260/586 P |
| 3,093,686 | 6/1963 | Simon et al. | 260/586 P |
| 3,530,185 | 9/1970 | Pugi | 260/610 B |
| 3,598,869 | 9/1971 | Volpe et al. | 260/586 R |

FOREIGN PATENTS OR APPLICATIONS

| | | | |
|---|---|---|---|
| 777,087 | 6/1957 | United Kingdom | 260/586 P |

Primary Examiner—Norman Morgenstern

[57] ABSTRACT

The process of oxidizing cyclohexane to produce cyclohexanone and cyclohexanol in the weight ratio of 0.5 to 1.5 of cyclohexanone to cyclohexanol, said process comprising contacting a stream of liquid cyclohexane with oxygen in each of at least three successive oxidation stages by introducing into each stage a mixture of gases comprising molecular oxygen and inert gas, said oxygen being introduced in amounts that may range from an amount that will substantially all react with the cyclohexane under the particular conditions involved to an amount in excess of the amount required to react with the cyclohexane, said excess being such that the overall oxygen consumed in the oxidation zone is not more than 95 mole percent of the amount fed under the particular conditions involved, in the presence of a binary catalyst system comprising 0.02 to 0.9 ppm chromium and 0.1 to 5 ppm cobalt at a temperature of from 130° to 200° C. and a pressure of from 60 to 350 psig, reacting any cyclohexylhydroperoxide that may be formed in the presence of said binary catalyst system and recovering a product of cyclohexanone and cyclohexanol in the above ratio.

4 Claims, 1 Drawing Figure

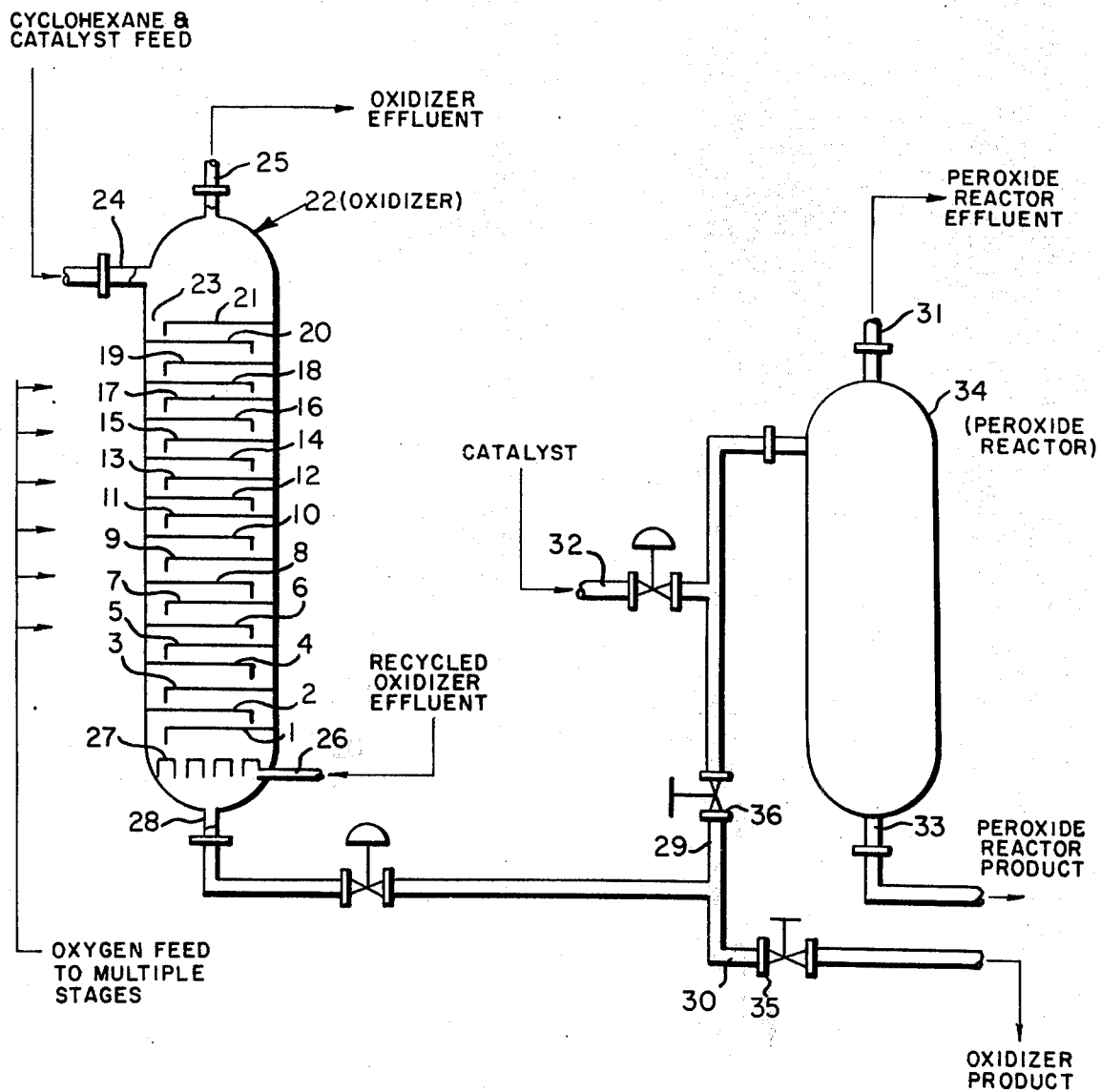

CYCLOHEXANE OXIDATION IN THE PRESENCE OF BINARY CATALYSTS

BACKGROUND OF THE INVENTION

1. Field of the Invention

This invention relates to a process for oxidizing cyclohexane with air whereby adipic acid precursors are prepared which permit improved yield of adipic acid. More specifically, this invention relates to a process for oxidizing cyclohexane with air to obtain adipic acid precursors by conducting said oxidation in the presence of a binary catalyst system of chromium and cobalt compounds.

2. Description of the Prior Art

In U.S. Pat. No. 3,530,185 there is disclosed a process for manufacturing precursors of adipic acid by oxidation of cyclohexane with an oxygen-containing inert gas which process is conducted at elevated temperature and pressure by contacting a stream of liquid cyclohexane at each of several successive stages of an oxidation zone with a mixture of gases including molecular oxygen at controlled partial pressure and inert gas; causing said mixtures of gases to pass countercurrent to the stream of cyclohexane; and recovering the stream of cyclohexane containing partial oxidation products of cyclohexane from the last of said stages. The useful partial oxidation products of cyclohexane, i.e. adipic acid precursors, which are the primary products of said process comprise cyclohexanol and cyclohexanone. Under the conditions of this process, conversion to by-products such as dicarboxylic acid and monocarboxylic acids is minimized.

In U.S. application Ser. No. 365,225, filed May 30, 1973 there is disclosed a process for the oxidation of cyclohexane to a product fluid consisting essentially of unreacted cyclohexane, cyclohexanone, cyclohexanol and a high proportion of cyclohexyl hydroperoxide, the product fluid being substantially free of peroxides other than cyclohexylhydroperoxide. This process comprises oxidizing cyclohexane containing a cobalt catalyst in a series of zones wherein cyclohexane is fed countercurrent to an oxidizing gas containing molecular oxygen, the amount of oxygen present in each reaction zone being in excess of that which will react under the particular conditions of that zone. The catalyst level required is from about 0.1 to 5 ppm based on the product fluid defined as the fluid recovered exiting the lowest oxidation zone and containing cyclohexane, cyclohexanol, cyclohexanone, cyclohexylhydroperoxide and other oxidation products in minor amounts. More catalyst than 5 ppm cobalt results in significantly lower amounts of cyclohexylhydroperoxide. At catalyst levels lower than 0.1 ppm the reaction becomes inefficient in that by-products including peroxides other than cyclohexylhydroperoxide are produced while lowering productivity of the desired products.

SUMMARY OF THE INVENTION

Now it has been discovered that the yield and quality of adipic acid produced from precursors for adipic acid are improved when the weight ratio of cyclohexanone to cyclohexanol in the precursors is in the range of from 0.5 to 1.5 (preferably 0.5 to 1.0). This weight ratio of cyclohexanone to cyclohexanol is obtained according to the process of this invention by utilizing a binary catalyst system comprising 0.02 to 0.90 ppm chromium and 0.1 to 5 ppm cobalt.

Thus the process of the present invention comprises a process for the preparation of cyclohexanone and cyclohexanol in the weight ratio of from 0.5 to 1.5 (preferably 0.5 to 1.0) by contacting a stream comprising liquid cyclohexane with oxygen at each of at least three successive oxidation stages by introducing into each stage a mixture of gases comprising molecular oxygen and inert gas, said oxygen being introduced in amounts that may range from the stoichiometric amount required to react with the cyclohexane under the particular conditions involved to an amount in excess of the amount required to react with the cyclohexane, in the presence of a binary catalyst system comprising 0.02 to 0.9 ppm chromium and 0.1 to 5 ppm cobalt at a temperature of from 130° to 200° C. and a pressure of from 60 to 350 psig (preferably 110–200 psig) converting peroxides, if any, and recovering a product consisting essentially of cyclohexanol and cyclohexanone.

What is meant by the amount referred to above as an excess of the oxygen required to react with the cyclohexane is that the excess oxygen fed is such that the overall amount of oxygen consumed in the oxidizing zone is not more than 95 mole percent of the amount fed to the stages under the conditions of the stages. Thus all the oxygen fed is not reacted. What is meant by the stoichiometric amount required to react with the cyclohexane under the particular conditions involved is the reacting of substantially all the oxygen fed. Thus the amount fed may vary widely according to the temperature, the holdup time in the oxidation zone and the amount of catalyst used.

What is meant by stages versus zones in this application is that stages are a subdivision of a zone. For example, an oxidation zone may have several oxidation stages.

The process for the oxidation of cyclohexane to form the precursors for the preparation of adipic acid in the weight ratio of the present invention is achieved by a variety of processes wherein the binary catalyst system of this invention is utilized.

One such process for the preparation of the precursors for adipic acid involves the oxidation of cyclohexane to produce a product fluid consisting essentially of unreacted cyclohexane, cyclohexanone, cyclohexanol, and cyclohexylhydroperoxide, the percentage of cyclohexylhydroperoxide to the total of cyclohexanone, cyclohexanol and cyclohexylhydroperoxide being greater than 15% by weight, the product fluid being substantially free of peroxides other than cyclohexylhydroperoxide, said process comprising passing a fluid containing cyclohexane and a cyclohexane soluble binary catalyst system downwardly through a series of oxygen cleanup stages and oxidizing stages at a pressure measured at the top of the oxygen cleanup zone of 60–350 psig while countercurrently passing an oxidizing gas containing molecular oxygen upwardly through the zones, the fluid initially passing through a series of oxygen cleanup stage wherein the temperature is maintained in the range of 130° to 180° C. and where the oxygen concentration in the upward passing gas leaving the oxygen cleanup zone is reduced to less than four mole percent, the fluid then passing through a series of oxidizing stages operated at a temperature in the range of 140°–170° C. in which the level of oxygen is maintained at a level in excess of the amount of oxygen that will react with the fluid mixture under the particular conditions of that zone by addition of oxidizing gas to that zone, the overall amount of oxygen consumed in the oxidizing zone being not more than 95 mole percent of the amount fed; and passing the product fluid containing cyclohexane, cyclohexanol, cyclohexanone and cyclohexylhydroperoxide obtained from the exit of the lowest oxidizing stage through a peroxide reaction zone in the presence of the binary catalyst system of this invention and recovering a product wherein the cyclohexanone to cyclohexanol weight ratio is 0.5 to 1.5.

The detailed description of the process for the oxidation of cyclohexane to form a product fluid containing cyclohexane, cyclohexanol, cyclohexanone and cyclohexylhydroperoxide is disclosed in application Ser. No. 365.225, filed May 30, 1973 which disclosure is hereby incorporated by reference in the present application.

A second process for the preparation of the precursors for adipic acid comprises oxidation of cyclohexane in the presence of the binary catalyst system of the present invention by introducing a stream comprising preheated liquid cyclohexane into the first of at least three successive oxidation stages; said liquid cyclohexane being maintained at a temperature of 130°–200° C. and the pressure in the oxidation stages being in the range of 60–350 psig; said stages being vertically positioned and arranged such that the liquid discharged from an upper stage is received in the next lower stage and at a rate such that the average liquid residence time in said stage is in the range 0.54–5.3 minutes; introducing air in the lower portion of each of said stages in an amount such that the ratio of the volume of gaseous oxygen to the total gas-free liquid volume in said stage is in the range 2.9–60 hr.$^{-1}$, diluting said air with inert gas, causing said diluted air to pass countercurrent to said liquid in each stage, maintaining the conditions such that substantially all of the oxygen introduced into each stage is consumed in that stage, causing the total inert gas to pass countercurrent to said liquid through all preceding higher oxidation stages and thereafter recovering a product containing cyclohexanone and cyclohexanol in the weight ratio of 0.5 to 1.5 cyclohexanone to cyclohexanol.

Details of this second process are disclosed in U.S. Pat. No. 3.530,185 which disclosure is hereby incorporated by reference in the present application. Thus the process of the present invention is an improvement over the process in U.S. Pat. No. 3,530,185 whereby cyclohexane is oxidized in the presence of the binary catalysts of this invention.

A third process for the preparation of the precursors for adipic acid applicable to the invention involves first the oxidation of cyclohexane to produce a product fluid containing cyclohexane, cyclohexanol, cyclohexanone and cyclohexylhydroperoxide according to the process disclosed in U.S. application Ser. No. 365,225 followed by further treatment of the product fluid in the presence of a binary catalyst system comprising from 0.02 to 0.9 ppm of chromium and from 0.1 to 5 ppm of cobalt to react the hydroperoxide with cyane and to form cyclohexanol and cyclohexanone to yield an overall cyclohexanone to cyclohexanol weight ratio of 0.5 to 1.5. Thus the third process for the preparation of precursors for adipic acid wherein the cyclohexanone to cyclohexanol weight ratio is from 0.5 to 1.5 comprises first oxidizing cyclohexane to produce a product fluid consisting essentially of unreacted cyclohexane, cyclohexanone, cyclohexanol, and cyclohexylhydroperoxide, the percentage of cyclohexylhydroperoxide to the total of cyclohexanone, cyclohexanol and cyclohexylhydroperoxide being greater than 15% by weight, the product fluid being substantially free of peroxides other than cyclohexylhydroperoxide, by passing a fluid containing cyclohexane and a cyclohexane soluble cobalt salt in the amounts of 0.1 to 5 ppm of product fluid downwardly through a series of oxygen cleanup stages and oxidizing stages at a pressure measured at the top of the oxygen cleanup zone of 60–350 psig while countercurrently passing an oxidizing gas containing molecular oxygen upwardly through the stages, the fluid initially passing through a series of oxygen cleanup stages wherein the temperature is maintained in he range of 130° to 180° C. and where the oxygen concentration in the upward passing gas leaving the oxygen cleanup zone is reduced to less than four mole percent, the fluid then passing through a series of oxidizing stages operated at a temperature in the range of 140°–170° C. in which the level of oxygen is maintained at a level in excess of the amount of oxygen that will react with the fluid mixture under the particular conditions of that zone by addition of oxidizing gas to that zone, the overall amount of oxygen consumed in the oxidizing zone being not more than 95 mole percent of the amount fed; and second reacting the product fluid containing cyclohexane, cyclohexanol, cyclohexanone and cyclohexylhydroperoxide in a peroxide reaction zone in the presence of the binary catalyst system of this invention.

The binary catalyst system of the present invention comprises cobalt and chromium compounds that are soluble in the liquid cyclohexane to be oxidized. Representative examples of cobalt and chromium compounds of the invention include cobalt and chromium salts of carboxylic acids and salts of organic acids produced in the course of the cyclohexane oxidation. Representative examples of cobalt salts of carboxylic acids include cobalt naphthenate, cobalt octoate, cobalt laurate, cobalt palmitate, cobalt stearate, cobalt linoleate and cobalt acetylacetonate. Representative examples of chromium salts of carboxylic acids include chromium naphthenate, chromium octoate, chromium laurate, chromium palmitate, chromium stearate, chromium linoleate and chromium acetylacetonate. Representative examples of organic acids that are produced in the course of the cyclohexane oxidation include caproic, valeric, adipic, glutaric and hydroxycaproic acids.

The binary catalyst system of the present invention is used in the amounts ranging from 0.02 to 0.9 ppm of chromium and 0.1 to 5 ppm of cobalt, both as metals based on the total liquid stream exiting the bottom of the oxidation zone. Where the binary catalyst system of this invention is added to the peroxide reaction zone it is based on the total liquid stream exiting the oxidation zone since it then is fed to the peroxide reaction zone. The process of this invention involves the aforesaid total amount of catalyst. Thus where the binary catalyst is added to the oxidation zone and the peroxide reaction zone the total amount used is 0.02 to 0.9 ppm chromium and 0.1 to 5 ppm cobalt, both as metals.

Any conversion level of cyclohexane to attain the cyclohexanone/cyclohexanol ratios of this invention are operable when substantially all the oxygen fed is reacted. However 1 to 11% is preferred and 2 to 5% are most preferred.

In the case of excess oxygen referred to herein, in order to prepare the product fluid having at least 15% by weight cyclohexylhydroperoxide, as stated above, the conversion of cyclohexane to cyclohexanone/cyclohexanol should be 1 to 7%, preferably 2–5%.

As is illustrated in the accompanying Figure, cyclohexane containing the binary catalyst is first passed through an oxygen cleanup zone where the cyclohexane is contacted and reacted with the gas that has been previously reacted with cyclohexane in the oxidation zone. The oxygen cleanup zone is operated at a temperature in the range of 130° to 180° C. and at a pressure of 60 to 350 psig as measured at the top of the cleanup zone. In the oxygen cleanup zone most of the oxygen remaining in the gas that had previously contacted and reacted with cyclohexane in the oxidizing zone reacts further with cyclohexane so that the gas leaving the top of the reactor contains only a very low concentration of oxygen. The oxygen concentration in this off-gas measured after the cyclohexane condensation should be less than 4 mole percent so that the gas will not form an explosive mixture.

After passing through the oxygen cleanup zone, the cyclohexane passes into a series of oxidizing stages or an oxidation zone. These stages are maintained at a temperature in the range of 140° to 170° C. and since they are in the same reactor as the oxygen cleanup zone the pressure is in the same range as the oxygen cleanup zone: 60–350 psig, as measured at the top of the cleanup zone. The temperature may vary from one oxidizing stage to another. In each oxidizing stage the concentration of the oxygen in the gas is kept at the desired level by adding the oxidation gas, usually air, at each stage.

In the oxidizing zone the concentration of the oxygen in the inert gas is kept in excess of an amount that will react with the cyclohexane feed in that stage. No more than 95% of the total oxygen fed to the oxidizing zone should be consumed in the oxidizing zone.

When substantially all of the oxygen fed to the oxidation zone is consumed, the product leaving the oxidation zone contains primarily cyclohexanone and cyclohexanol in the ratios of the present invention.

When an excess of oxygen is used the product fluid leaving the oxidation zone will contain cyclohexane, cyclohexanol, cyclohexanone, cyclohexylhydroperoxide and other oxidation products in minor amounts, but substantially no peroxides other than cyclohexylhydroperoxide. The percentage by weight of cyclohexylhydroperoxide to the total cyclohexanol, cyclohexanone and cyclohexylhydroperoxide as measured at the exit of the lowest oxidizing stage will be greater than 15%. The stream leaving the oxidizer then passes into a peroxide reactor where more binary catalyst may be added such that the overall binary catalyst added to the oxidation zone and the peroxide reactor is 0.02 to 0.9 ppm of chromium and 0.1 to 5 ppm of cobalt to form cyclohexanone, cyclohexanol and other products in minor amounts to attain the ratio of cyclohexanone to cyclohexanol of this invention.

The ratio of cyclohexanone to cyclohexanol of this invention may also be attained by first passing cyclohexane containing a soluble cobalt catalyst through a series of stages of oxygen cleanup where the cyclohexane is contacted and reacted with the gas that has been previously reacted with cyclohexane in the oxidation zone. The oxygen cleanup zone is operated at a temperature in the range of 130° to 180° C. and at a pressure of 60 to 350 psig as measured at the top of the cleanup zone. In the oxygen cleanup zone most of the oxygen remaining in the gas that had previously contacted and reacted with cyclohexane in the oxidizing zone reacts further with cyclohexane so that the gas leaving the top of the reactor contains only a very low concentration of oxygen. The oxygen concentration in this off-gas measured after the cyclohexane condensation should be less than 4 mole percent so that the gas will not form an explosive mixture.

After passing through the oxygen cleanup zone, the cyclohexane passes into a series of oxidizing stages or an oxidation zone. This zone is maintained at a temperature in the range of 140° to 170° C. and since both the cleanup and oxidation zones are in the same reactor the pressure is in the same range as the oxygen cleanup zone; 60–350 psig as measured at the top of the cleanup zone. The temperature may vary from one oxidizing stage to another. In the oxidizing zone the concentration of the oxygen in the gas is kept at a level in excess of the amount of oxygen that will react with the cyclohexane feed in that zone; this is accomplished by adding the oxidation gas, usually air, at each stage. In addition, no more than 95% of the total oxygen fed to the oxidizing zone should be consumed in the oxidizing zone.

After passing through the oxidizing zone, the product fluid is recovered. The product fluid will contain in addition to cyclohexane, cyclohexanol, cyclohexanone, cyclohexylhydroperoxide, other oxidation products in minor amounts, but substantially no peroxides other than cyclohexylhydroperoxide. The percentage by weight of cyclohexylhydroperoxide to the total of cyclohexanol, cyclohexanone and cyclohexylhydroperoxide as measured at the exit of the lowest oxidizing stage will be greater than 15%. The product fluid then passes into a peroxide reactor where cyclohexylhydroperoxide is reacted in the presence of the binary catalyst such that the overall amount of catalyst added to the oxidation zone and to the peroxide reactor is 0.02 to 0.9 ppm of chromium and 0.1 to 5 ppm of cobalt to form cyclohexanone, cyclohexanol and other products in minor amounts to attain the ratio of cyclohexanone to cyclohexanol of this invention.

While the inert gas is usually nitrogen, it may be any gas or vapor which cannot itself react with cyclohexane or its oxidation products or be substantially oxidized under the conditions of the oxidation reaction. Moreover, at least some inert gas entering the oxidation zone must be unsaturated with respect to cyclohexane and preferably be substantially unsaturated with respect to cyclohexane so that liquid cyclohexane may evaporate and be transported by the inert gas as the inert gas passes from a later stage to an earlier stage (relative to the flow of liquid), and the concentration of the useful oxidation products within the remaining liquid cyclohexane in successive stages of the oxidation zone is increased in consequence.

The oxidation zone must be arranged in such a way that several successive stages are provided at each of which successive stages the stream of cyclohexane can be contacted with oxygen. At least three such successive stages will be required and from five to thirty such successive stages will usually be considered adequate for practicing the process of the present invention. Mainly considerations relative to the size of the total reactor place restrictions upon the maximum number of such successive stages within the oxidation zone. It will be understood that the concentration of partial oxidation products of cyclohexane within the stream of cyclohexane in general increases at each such successive stage.

It will be appreciated that the process of the present invention may be carried out in any type of multistaged countercurrent vapor-liquid contacting device such as in stirred autoclaves, tower reactors or tubular reactors. Best results, from the standpoint of economics, are obtained when the process of the present invention is carried out in a staged tower reactor. Such a staged tower reactor may contain within the reactor shell the various zones, all in contiguous relationship, and each such zone may itself be subdivided by a series of stages.

A unique feature of this invention is that specific quantities of chromium can unexpectedly change a normal cobaltcatalyzed cyclohexane oxidation by modifying the distribution of oxidation products in such a way as to improve the yield, quality and production rate in the manufacture of adipic acid by the use of these oxidation products.

The action of trace amounts of chromium in conjunction with cobalt is unique in that by proper selection of the chromium limits the product formation can be controlled in two specific ways, which is of great commercial significance: (1) control of the ratio of cyclohexanone to cyclohexanol to ratios that have been found will cause an increase in adipic acid yield in the subsequent nitric acid oxidation of said product, and (2) reduction in the formation of certain by-products which adversely affect adipic acid quality.

In the manufacture of adipic acid not only is the yield of adipic acid important, but also the quality or purity of the adipic acid. This is because quality is critical for uses such as nylon production. One of the major factors that can affect adipic acid quality is the quantity of certain by-products produced in the cyclohexane oxidation. Two particularly troublesome by-products which can contaminate the cyclohexanone-cyclohexanol mixture are caproic acid and cyclohexen-1-ol. Removal of these contaminants from either the mixture of cyclohexanone and cyclohexanol product from the oxidation of cyclohexane or of their products formed in the nitric acid oxidation can be difficult and costly. In many instances, the production capacity is severely limited by the inefficiency in removing these impurities. The process of this invention offers an improved solution to this problem by preventing or reducing the formation of these and other related impurities in the cyclohexane oxidation step. This can significantly reduce the investment and the amount of energy required to manufacture adipic acid.

To illustrate the importance of cyclohexanone/cyclohexanol ratio on yield nitric acid oxidation of various weight ratios of cyclohexanone to cyclohexanol were used to produce adipic acid. The nitric acid oxidation was conducted in a reactor and holdup receiver of 2-inch diameter glass pipe at 85° C. and 40 psig pressure. Approximately 135 grams of nitric acid, 163.4 grams of water, 0.12 gram vanadium, 1.5 grams copper and 26 grams of adipic acid were charged to the reactor. The reactor system was purged with nitrogen before oxidation was initiated. Selected mixtures of cyclohexanone-cyclohexanol were pumped continuously beneath the surface of the magnetically stirred reaction liquid. Approximately 0.45 mole of organic feed was reacted in a one-hour period. Makeup nitric acid in a concentration of 55 weight percent nitric acid, 0.04 weight percent vanadium and 0.5 weight percent copper with the balance being water was pumped into the reactor at a rate of 5.8 ml/min. The liquid in the reactor was maintained at 85° C. and the liquid in the holdup receiver was held at 107°–110° C. during the hour in which the cyclohexanone-cyclohexanol was fed to the reactor. At the end of one hour, the contents of the reactor was heated to 100° C. for 10 minutes. The reaction product was cooled and then analyzed by liquid-liquid column chromatography to determine the amount of adipic acid produced and the molar adipic acid yield. The following table summarizes the data obtained:

TABLE I

| Wt. Ratio Cyclohexanone to Cyclohexanol in the Organic Feed | Adipic Acid Yield % |
| --- | --- |
| 4 | 94.6 |
| 1.5 | 95.2 |
| 1.0 | 95.2 |
| 0.67 | 95.3 |
| 0.43 | 94.7 |
| 0.25 | 94.4 |
| 0.10 | 94.4 |
| 0 | 93.8 |

The process of the present invention has utility in the preparation of intermediates of adipic acid which is useful in the preparation of nylon.

DESCRIPTION OF PREFERRED EMBODIMENTS

In the examples which follow a system such as that illustrated in the Figure was used unless otherwise indicated. The reactor 22, made of any suitable material such as 316 stainless steel, contains 21 equally spaced trays designated 1–21. The reactor height to diameter ratio is 8, and the downcomer opening 23 cross-sectional area for each tray to tower cross-sectional area is 0.12. The tower has inlet port 24 through which cyclohexane containing catalyst is introduced into the reactor, and off-gas port 25 through which the gaseous vapor containing relatively small amounts of oxygen is removed from the reactor. The catalyst may also be introduced at one or more other points in the oxygen cleanup zones. Each tray 1–21 contains a number of apertures (not shown) through which the oxidizing gas passes on way up the tower. Oxidizing gas may be fed to any or all of the first 18 trays. Since each tray must accommodate not only the gas fed to it alone but also gases from the trays below, the number and/or size of the apertures is progressively greater from the bottom to the top of the reactor. The average free tray area (i.e., the area of the apertures in the trays) for all of the trays to tower cross-sectional area may vary widely but for the examples set forth below it is 1.2% calculated according to the following equation:

$$\frac{\text{Average free tray area} \times 100}{\text{Tower cross-sectional area}} = 1.2\%$$

Recycled off-gas after removal of most of the contained cyane, K and A is introduced through inlet 26 through spargers 27. Outlet port 28 is used to remove the product continuously from the reactor. Sampling devices (not shown) to sample the gas or liquid may be inserted through reactor if desired, at selected locations.

In operation the cyclohexane to be oxidized is introduced through inlet 24. It passes over tray 21 and the gas under tray 21 bubbles through the holes in tray 21 and through the cyclohexane. This flow across each tray while being subjected to the gas treatment is repeated as the cyclohexane moves down the tower.

If desired, the oxidizing gas feed may be shut off at trays lower than tray 18, and thus increases the length of the oxygen cleanup zone.

Recycled gas is introduced at 26 through sparger 27 to increase the volume of gas moving up the tower and thus providing mild oxidizing conditions throughout the tower, while at the same time stripping cyclohexane from the product fluid.

The product flow from the oxidation zone exits through outlet 28 and is either passed on to further refining through line 30 and valve 35 where the product flow contains the ratio of cyclohexanone and cyclohexanol of this invention or passes through line 29 to the peroxide reactor 34. Gases from the peroxide reactor exit via line 31. Catalyst is added to the flow to reactor 34 via line 32. Product from the peroxide reactor having the ratio of cyclohexanone to cyclohexanol of this invention exits the peroxide reactor via line 33.

The following examples further illustrate the invention:

EXAMPLE 1–2

To a tower oxidizer substantially as described above was fed cyclohexane with a cobalt naphthenate and chromium naphthenate catalyst mixture and the cyclohexane oxidized according to the conditions in Table 2. A peroxide reactor, as described above, was used to react the cyclohexylhydroperoxide from the oxidizer under the conditions indicated in Table 2. Table 2 summarizes the results and includes a control run with cobalt alone.

TABLE 2

|  | Ex. 1 | Ex. 2 |
|---|---|---|
| Number Air Feed Trays | 18 | 18 |
| Actual Air Feed Trays | 1–18 | 1–18 |
| Ratio of $\frac{\text{Inert Gas Rate}}{\text{Product Effluent Rate}}$, $\left(\frac{\text{SCFH}}{\text{Lb per Hour}}\right)$ [1] | 0.22 | 0.22 |
| Ratio of $\frac{\text{Total Air Rate}}{\text{Product Effluent Rate}}$, $\left(\frac{\text{SCFH}}{\text{Lb per Hour}}\right)$ [2] | 0.58 | 0.58 |
| Product Effluent Rate, Parts per Hour [3] | 1778 | 1778 |
| Catalyst Concentration Added to Tray 21 of Tower Oxidizer | | |
| ppm Cobalt [4] | 0.10 | 0.10 |
| ppm Chromium [5] | 0 | 0.04 |
| Tower Oxidizer Pressure, psig [6] | 150 | 140 |
| Average Temperatures in Tower Oxidizer, °C. | | |
| Oxygen Cleanup Zone | 158.2 | 153.7 |
| Oxidation Zone [7] | 161.1 | 158.7 |
| Oxygen Concentration (mol % $O_2$ dry basis) Leaving Oxidation Zone [8] | 4.6 | 4.9 |
| Mol % Oxygen Consumed in Oxidation Zone | 73 | 71 |
| Weight % $\left(\frac{\text{cyclohexylhydroperoxide}}{\text{cyclohexylhydroperoxide + cyclohexanone + cyclohexanol}}\right)$ in Product Effluent from Tower Oxidizer | 45.6 | 39.1 |
| Catalyst Concentration in the Peroxide Reactor | | |
| ppm Cobalt [4] | 2.15 | 2.15 |
| ppm Chromium [5] | 0 | 0.86 |
| Peroxide Reactor Pressure, psig [6] | 100 | 95 |
| Average Temperature in Peroxide Reactor, °C. | 169.4 | 167.3 |
| Weight % cyclohexanone + cyclohexanol + cyclohexylhydroperoxide in Product Effluent from Peroxide Reactor [9] | 2.7 | 2.6 |
| Weight % $\left(\frac{\text{cyclohexylhydroperoxide}}{\text{cyclohexylhydroperoxide + cyclohexanone + cyclohexanol}}\right)$ in Product Effluent from Peroxide Reactor | 8.9 | 8.2 |
| Ratio cyclohexanone to cyclohexanol in Product Effluent from Peroxide Reactor $\left(\frac{\text{Lb}}{\text{Lb}}\right)$ | 0.46 | 0.57 |
| Ratio cyclohexen-1-ol to cyclohexanone + cyclohexanol in Product Effluent from Peroxide Reactor $\left(\frac{\text{Lb}}{100 \text{ Lb}}\right)$ [10] | 0.23 | 0.19 |

[1] Inert gas feed for these experiments is nitrogen.
[2] The total air is distributed equally to all the air feed trays.
[3] Weight flow of liquid leaving the bottom of the tower oxidizer.
[4] Parts of cobalt metal introduced as cobalt naphthenate per million parts of product effluent from tower oxidizer. Includes cobalt added to tower oxidizer.
[5] Parts of chromium metal introduced as chromium naphthenate per million parts of product effluent from tower oxidizer. Includes chromium added to tower oxidizer.
[6] Measured at top of the reactor.
[7] Defined as the zone where oxygen is fed.Lk6 [8] Dry basis concentration of oxygen is after removal of cyclohexane and other condensables.
[9] Product effluent rate from peroxide reactor is essentially the same as the product effluent rate from the tower oxidizer.
[10] Ratio is the net production of cyclohexen-1-ol to the net production of cyclohexanone to cyclohexanol.

EXAMPLES 3 to 5

The procedure of Examples 1–2 was followed except that only cobalt catalyst was added to the oxidizer and the cyclohexylhydroperoxide reaction was conducted in the presence of cobalt-chromium catalyst mixtures. The conditions and results are summarized in Table 3.

TABLE 3

|  | Ex. 3 | Ex. 4 | Ex. 5 |
|---|---|---|---|
| Number Air Feed Trays | 18 | 18 | 18 |
| Actual Air Feed Trays | 1–18 | 1–18 | 1–18 |
| Ratio of $\frac{\text{Inert Gas Rate}}{\text{Product Effluent Rate}}$, $\left(\frac{\text{SCFH}}{\text{Lb per Hour}}\right)$ [1] | 0.22 | 0.22 | 0.22 |

TABLE 3-continued

|  | Ex. 3 | Ex. 4 | Ex. 5 |
|---|---|---|---|
| Ratio of $\frac{\text{Total Air Rate}}{\text{Product Effluent Rate}}$ $\left(\frac{\text{SCFH}}{\text{Lb per Hour}}\right)$ [2] | 0.55 | 0.56 | 0.55 |
| Product Effluent Rate, Parts per Hour [3] | 1890 | 1869 | 1890 |
| Catalyst Concentration Added to Tray 21 of Tower Oxidizer | | | |
| ppm Cobalt [4] | 0.19 | 0.19 | 0.19 |
| ppm Chromium [5] | 0 | 0 | 0 |
| Tower Oxidizer Pressure, psig [6] | 145 | 140 | 142 |
| Average Temperatures in Tower Oxidizer, 2C. | | | |
| Oxygen Cleanup Zone | 166.3 | 164.1 | 164.9 |
| Oxidation Zone [7] | 161.9 | 159.6 | 160.4 |
| Oxygen Concentration (mol % $O_2$ dry basis) Leaving Oxidation Zone [8] | 4.6 | 5.3 | 5.1 |
| Mole % Oxygen Consumed in Oxidation Zone | 73 | 69 | 70 |
| Weight % $\left(\frac{\text{cyclohexylhydroperoxide}}{\text{cyclohexylhydroperoxide + cyclohexanone + cyclohexanol}}\right)$ in Product Effluent from Tower Oxidizer | 41.5 | 38.2 | 41.2 |
| Catalyst Concentration in the Peroxide Reactor | | | |
| ppm Cobalt [4] | 2.12 | 0.19 | 0.29 |
| ppm Chromium [5] | 0 | 0.83 | 0.77 |
| Peroxide Reactor Pressure, psig [6] | 90 | 90 | 90 |
| Average Temperature in Peroxide Reactor, °C. | 165.5 | 164.7 | 162.9 |
| Weight % cyclohexanone + cyclohexanol + cyclohexylhydroperoxide in Product Effluent from Peroxide Reactor [9] | 3.1 | 3.4 | 2.9 |
| Weight % $\left(\frac{\text{cyclohexylhydroperoxide}}{\text{cyclohexylhydroperoxide + cyclohexanone + cyclohexanol}}\right)$ in Product Effluent from Peroxide Reactor | 5.5 | 3.6 | 7.6 |
| Ratio cyclohexanone to cyclohexanol in Product Effluent from peroxide Reactor $\left(\frac{Lb}{Lb}\right)$ | 0.48 | 0.61 | 0.70 |
| Ratio cyclohexen-1-ol to cyclohexanone + cyclohexanol in Product Effluent from Peroxide Reactor $\left(\frac{Lb}{100\ Lb}\right)$ [10] | 0.26 | 0.14 | 0.17 |

[1] Inert gas feed for these experiments is nitrogen.
[2] The total air is distributed equally to all the air feed trays.
[3] Weight flow liquid the bottom of the tower oxidizer.
[4] Parts of cobalt metal introduced as cobalt naphthenate per million parts of product effluent from tower oxidizer. Includes cobalt added to tower oxidizer.
[5] Parts of chromium metal introduced as chromium naphthenate per million parts of product effluent from tower oxidizer. Includes chromium added to tower oxidizer.
[6] Measured at top of the reactor.
[7] Defined as the zone where oxygen is fed.
[8] Dry basis concentration of oxygen is after removal of cyclohexane and other condensables.
[9] Product effluent rate from peroxide reactor is essentially the same as the product effluent from the tower oxidizer.
[10] Ratio is the net production of cyclohexen-1-ol to the net production of cyclohexanone to cyclohexanol.

We claim:

1. A process for the preparation of cyclohexanone and cyclohexanol in the weight ratio of from 0.5 to 1.5 ketone to alcohol by contacting a stream comprising liquid cyclohexane with oxygen at each of at least three successive oxidation stages by introducing into each stage a mixture of gases comprising molecular oxygen and inert gas, said oxygen being introduced in an amount in excess of the stoichiometric amount required to react with the cyclohexane, wherein the overall amount of oxygen consumed is not more than 95 mole percent of the amount fed to the stages under the particular conditions of the stages, in the presence of a binary catalyst system comprising chromium and cobalt as compounds which are soluble in cyclohexane at a temperature of from 130° to 180° C. and a pressure of from 60 to 350 psig to produce a first product stream comprising unreacted cyclohexane, cyclohexanone, cyclohexanol, and cyclohexylhydroperoxide; forwarding the first product stream to a deperoxidation operation, wherein the cyclohexylhydroperoxide present in the first product stream is decomposed in the presence of said binary catalyst system, to form additional quantities of cyclohexanone and cyclohexanol, the overall amount of catalyst being in the range of 0.02 to 0.9 ppm chromium and 0.1 to 5 ppm cobalt; and recovering a product consisting essentially of cyclohexanone and cyclohexanol.

2. The process of claim 1 wherein the weight ratio of cyclohexanone to cyclohexanol is 0.5 to 1.0.

3. A process for the preparation of cyclohexanone and cyclohexanol in a weight ratio of from 0.5 to 1.5 ketone to alcohol which comprises first oxidizing cyclohexane to produce a first product fluid consisting essentially of unreacted cyclohexane, cyclohexanone, cyclohexanol, and cyclohexylhydroperoxide, the percentage of cyclohexylhydroperoxide to the total of cyclohexanone, cyclohexanol and cyclohexylhydroperoxide being greater than 15% by weight, the first product fluid being substantially free of peroxides other than cyclohexylhydroperoxide, which comprises passing a fluid containing cyclohexane and a cyclohexane soluble cobalt salt in an amount of from 0.1 to 5 ppm of said product fluid downwardly through an oxygen cleanup zone comprising a series of oxygen cleanup stages and an oxidizing zone comprising a series of oxidizing stages at a pressure, measured at the top of the oxygen cleanup zone of 60–350 psig, while countercurrently passing an oxidizing gas containing molecular oxygen upwardly through the zones, the fluid initially passing through each series of oxygen cleanup stages wherein the temperature is maintained in the range of 130°–180° C. and where the oxygen concentration in the upward passing gas leaving the oxygen cleanup zone is reduced to less than four mole percent, the fluid then passing through said series of oxidizing stages operated at a temperature in the range of 140°–170° C. in which the level of oxygen is maintained at a level in excess of the amount of oxygen that will react with the fluid mixture by addition of oxidizing gas, the overall amount of oxygen consumed in the oxidizing zone being not more than 95 mole percent of the amount fed; second reacting the first product fluid containing cyclohexane, cyclohexanol, cyclohexanone and cyclohexylhydroperoxide in the presence of 0.02 to 0.9 ppm chromium and 0.1 to 5 ppm cobalt in a peroxide reactor to produce additional quantities of cyclohexanone and cyclohexanol; followed by recovering a product consisting essentially of cyclohexanone and cyclohexanol.

4. The process of claim 3 wherein the ratio of cyclohexanone to cyclohexanol is from 0.5 to 1.0.

* * * * *